US009585589B2

(12) United States Patent
McNair

(10) Patent No.: US 9,585,589 B2
(45) Date of Patent: Mar. 7, 2017

(54) COMPUTERIZED SYSTEMS AND METHODS FOR STABILITY-THEORETIC PREDICTION AND PREVENTION OF SUDDEN CARDIAC DEATH

(75) Inventor: Douglas S. McNair, Leawood, KS (US)

(73) Assignee: Cerner Innovation, Inc., Kansas City, KS (US)

( * ) Notice: Subject to any disclaimer, the term of this patent is extended or adjusted under 35 U.S.C. 154(b) by 724 days.

(21) Appl. No.: 12/982,625

(22) Filed: Dec. 30, 2010

(65) Prior Publication Data

US 2011/0190650 A1 Aug. 4, 2011

Related U.S. Application Data

(60) Provisional application No. 61/291,657, filed on Dec. 31, 2009.

(51) Int. Cl.
*A61B 5/0452* (2006.01)
*A61B 5/00* (2006.01)
*A61B 5/11* (2006.01)

(52) U.S. Cl.
CPC .............. *A61B 5/0452* (2013.01); *A61B 5/00* (2013.01); *A61B 5/0004* (2013.01);
(Continued)

(58) Field of Classification Search
CPC . A61B 5/0452; A61B 5/0464; A61B 5/04012; A61B 5/0468; A61B 5/0006; A61B 5/0472; A61B 5/7275
(Continued)

(56) References Cited

U.S. PATENT DOCUMENTS 5,419,338 A   5/1995 Sarma et al.
6,324,423 B1  11/2001 Callahan et al.
(Continued)

OTHER PUBLICATIONS

Ackerman M, Nemec, Jan, Hejlik, Joseph, Shen, Win-Kuang. Catecholamine-induced T-wave lability in congenital long QT syndrome: a novel phenomenon associated with syncope and cardiac arrest. Mayo Clin Proc. 2003;78:40-50.
(Continued)

*Primary Examiner* — Michael Kahelin
*Assistant Examiner* — Minh Duc Pham
(74) *Attorney, Agent, or Firm* — Shook, Hardy & Bacon L.L.P.

(57) ABSTRACT

Systems, methods and computer-readable media are provided for automatic identification of patients according to near-term risk of ventricular arrhythmias and sudden cardiac death (SCD). Embodiments of the invention are directed to event prediction, risk stratification, and optimization of the assessment, communication, and decision-making to prevent SCD, and in one embodiment take the form of a platform for wearable, mobile, unteathered monitoring devices with embedded decision support. Thus embodiments relate to automatically identifying persons at risk for arrhythmias and SCD through the use of noninvasive, portable, wearable electronic device and sensors equipped with signal-processing software and statistical predictive algorithms that calculate stability-theoretic measures derived from the digital electrocardiogram timeseries acquired by the device. The measurements and predictive algorithms embedded within the device provide for unsupervised use in the home or in general acute-care and chronic-care venues and afford a degree of robustness against variations in individual anatomy and sensor placement.

16 Claims, 8 Drawing Sheets

(52) U.S. Cl.
CPC .......... *A61B 5/1117* (2013.01); *A61B 5/6831* (2013.01); *A61B 5/6891* (2013.01); *A61B 5/6898* (2013.01); *A61B 5/7203* (2013.01); *A61B 5/7264* (2013.01); *A61B 5/7275* (2013.01); *A61B 5/742* (2013.01); *A61B 5/7405* (2013.01); *A61B 5/746* (2013.01); *A61B 5/747* (2013.01)

(58) Field of Classification Search
USPC .................................. 600/59, 509, 515–518
See application file for complete search history.

(56) References Cited

U.S. PATENT DOCUMENTS

| | | | |
|---|---|---|---|
| 6,821,256 | B2 | 11/2004 | Ackerman et al. |
| 6,835,176 | B2 | 12/2004 | McNair |
| 6,847,840 | B2 | 1/2005 | DePasquale et al. |
| 6,997,882 | B1 | 2/2006 | Parker et al. |
| 7,258,667 | B2 | 8/2007 | McNair |
| 7,423,537 | B2 | 9/2008 | Bonnet et al. |
| 7,477,936 | B2 | 1/2009 | Hardahl et al. |
| 7,479,890 | B2 | 1/2009 | Lehrman et al. |
| 7,608,458 | B2 | 10/2009 | Soykan et al. |
| 7,672,716 | B1 * | 3/2010 | Koh ................... A61B 5/02405 600/515 |
| 2001/0004234 | A1 | 6/2001 | Petelenz et al. |
| 2002/0095095 | A1 | 7/2002 | Callahan et al. |
| 2004/0220635 | A1 * | 11/2004 | Burnes ................. A61N 1/3627 607/17 |
| 2004/0236235 | A1 | 11/2004 | Fujita et al. |
| 2005/0182305 | A1 | 8/2005 | Hendrich |
| 2005/0240086 | A1 | 10/2005 | Akay |
| 2007/0027369 | A1 | 2/2007 | Pagnacco et al. |
| 2007/0197881 | A1 | 8/2007 | Wolf et al. |
| 2007/0219455 | A1 * | 9/2007 | Wong ................. A61B 5/02405 600/515 |
| 2008/0009686 | A1 | 1/2008 | Hendrich |
| 2008/0045804 | A1 | 2/2008 | Williams |
| 2008/0081958 | A1 | 4/2008 | Denison et al. |
| 2009/0171227 | A1 | 7/2009 | Dziubinski et al. |
| 2009/0318779 | A1 | 12/2009 | Tran |
| 2009/0326401 | A1 * | 12/2009 | Jonckheere .......... A61B 5/0452 600/516 |
| 2009/0326595 | A1 * | 12/2009 | Brockway et al. ................ 607/3 |
| 2010/0261980 | A1 | 10/2010 | Peng et al. |
| 2010/0261982 | A1 | 10/2010 | Noury et al. |
| 2010/0286490 | A1 | 11/2010 | Koverzin |
| 2011/0112414 | A1 * | 5/2011 | Panescu ............. A61B 5/04011 600/509 |

OTHER PUBLICATIONS

Adachi K, et al. Risk stratification for sudden cardiac death in dilated cardiomyopathy using microvolt-level T-wave alternans. Jpn Circ J. 2001;65:76-80.
Al-Khatib S, et al. Preventing tomorrow's sudden cardiac death today: dissemination of effective therapies for sudden cardiac death prevention. Am Heart J. 2008;156:613-22.
Arking D, et al. Genomics in sudden cardiac death. Circ Res. 2004;94:712-23.
Badilini F, et al. Automatic analysis of cardiac repolarization morphology using Gaussian mesa function modeling. J Electrocardiol 2008; 41:588-94.
Brugada P, Brugada J. RBBB, persistent ST segment elevation, and sudden cardiac death: A distinct clinical and electrocardiographic syndrome. J Am Coll Cardiol 1992; 20:1391-6.
Cleland J, et al. Clinical trials update from ESC 2009: AAA, Rely, Protect, Active-I,CRT survey, German Pre-SCD II Registry, and MADIT-CRT. Eur J Heart Fail 2009; 11:1214-9.
Clements-Jewery H, et al. Druggable targets for sudden cardiac death prevention: lessons from the past and strategies for the future. Curr Opin Pharmacol. 2009;9:146-53.
Deniz H, et al. Cost-benefit analysis of primary prevention of sudden cardiac death with an implantable cardioverter defibrillator versus amiodarone in Canada. Curr Med Res Opin. 2009;25:617-26.
Drezner J. Contemporary approaches to the identification of athletes at risk for sudden cardiac death. Curr Opin Cardiol. 2008;23:494-501.
Epstein A. Update on primary prevention implantable cardioverter-defibrillator therapy. Curr Cardiol Rep. 2009;11:335-42.
Fozzard H. After-depolarizations and triggered activity. Basic Res Cardiol. 1992;87(Suppl2):105-13.
Fuller M. Estimates of repolarization dispersion from electrocardiographic measurements. Circulation. 2000; 102:685-91.
Gimeno M, et al. Excercise-induced ventricular arrhythmias and risk of SCD in patients with hypertrophic cardiomyopathy. Eur Heart J. 2009; 30:2599-605.
Goldberger A, West B. Applications of nonlinear dynamics to clinical cardiology. Ann New York Acad Sci. 1987;504:155-212.
Hui Y, et al. A new algorithm of QT interval measurement on multiscale morphological derivative transform. IEEE Internaltion Sem Fut Biomed Info Eng, 2008.
Kamath G, Mittal S. The role of antiarrhythmic drug therapy for the prevention of sudden cardiac death. Prog Cardiovasc Dis. 2008;50:439-48.
Kautzner J. QT interval measurements. Cardiac Electrophysiol Rev. 2002; 6:273-7.
Kohler B, et al. The principles of software QRS Detection. IEEE Eng Med Biol. 2002; 21:42-57.
Laguna P, et al. New algorithm for QT interval analysis in 24-hour Holter ECG: Performance and applications. Med Biol Eng Comput 1990; 28:67-73.
Laitinen P, et al. Genes, exercise and sudden death: molecular basis of familial catecholaminergic polymorphic ventricular tachycardia. Ann Med. 2004;36(Suppl1):81-6.
Lakshmikantham V, et al. Vector Lyapunov Functions and Stability Analysis of Nonlinear Systems. Kluwer, 1991; pp. 1-172. (Hard Cover Book being mailed on Jul. 6, 2011).
Malik M, et al. Drug-induced Torsades de Pointes and implications for drug development. J Cardiovasc Electrophysiol. 2004; 15: 475-95.
Martinez J, et al. A wavelet-based ECG delineator: Evaluation on standard databases. IEEE Trans Biomed Eng. 52004; 51:570-81.
Monahan K, et al. Triggering of nocturnal arrhythmias by sleep-disordered breathing events. J Am Coll Cardiol 2009;54:1797-804.
Montagnana M, et al. Sudden cardiac death: prevalence, pathogenesis, and prevention. Ann Med. 2008;40:360-75.
Okin P, et al. Principal component analysis of the T wave and prediction of cardiovascular mortality in American Indians: The Strong Heart Study. Circulation. 2002; 105:714-9.
Osowski S, et al. Support vector machine-based expert system for reliable heartbeat recognition. IEEE Trans Biomed Eng. 2004; 51:582-9.
Paavola J, et al. Mutant ryanodine receptors in catecholaminergic polymorphic ventricular tachycardia generate delayed afterdepolarizations due to increased propensity to Ca2+ waves. Eur Heart J. 2007;28:1135-42.
Priori S, Napolitano C. Genetics of cardiac arrhythmias and sudden cardiac death. Ann N Y Acad Sci. 2004;1015:96-110.
Priori S, et al. Clinical and molecular characterization of patients with catecholaminergic polymorphic ventricular tachycardia. Circulation. 2002;106:69-74.
De Queiroz M, et al. Lyapunov-Based Control of Mechanical Systems. Birkhauser, 2000; pp. 1-316 (Hard Cover Book being mailed on Jul. 6, 2011).
Sabir I, et al. Risk stratification for sudden cardiac death. Prog Biophys Mol Biol. 2008;98:340-6.
Saumarez R, et al. Paced ventricular electrogram fractionation predicts sudden cardiac death in hypertrophic cardiomyopathy. Eur Heart J. 2008;29:1653-61.
Saxon L. udden cardiac death: epidemiology and temporal trends. Rev Cardiovasc Med. 2005;6(Suppl2):S12-20.
Sen-Chowdhry S, McKenna W. Sudden cardiac death in the young: a strategy for prevention by targeted evaluation. Cardiology. 2006;105:196-206.

(56) References Cited

OTHER PUBLICATIONS

Smith T, Cain M. Sudden cardiac death: epidemiologic and financial worldwide perspective. J Interv Card Electrophysiol. 2006;17:199-203.
Song Y, et al. An increase of late sodium current induces delayed afterdepolarizations and sustained triggered activity in atrial myocytes. Am J Physiol Heart Circ Physiol. 2008;294:H2031-9.
Stevenson W, Sweeney M. Arrhythmias and sudden death in heart failure. Jpn Circ J 1997;61:727-40.
U.S. NHLBI. What is sudden cardiac arrest? http://www.nhlbi.nih.gov/health/dci/Diseases/scda/scda_whatis.html http://www.nlm.nih.gov/medlineplus/news/fullstory_91890.html http://clinicaltrials.gov/ct2/show/NCT00064558.
Yap C, et al. Prediction of Torsade-causing potential of drugs by support vector machine approach. Tox Sci. 2004; 79:170-7.
Zabel M, et al. Practical use of T-wave morphology assessment. Cardiac Electrophysiology Rev. 2002; 6:316-22.
United States Patent and Trademark Office; Preinterview First Action Interview; U.S. Appl. No. 12/982,631; mailed Jan. 14, 2013, 21 pages.
First Action Interview Preinterview Communication dated Dec. 7, 2015 in U.S. Appl. No. 14/139,555, 7 pages.
Jackson, Irvin, "Side Effects of Zithromax, Other Antibiotics Linked to Heart Attack Risk: Study", Nov. 12, 2015, 7 pages. Available at: http://www.aboutlawsuits.com/zithromax-heart-study-3-89694/.
First Action Interview Office Action dated Apr. 8, 2016 in U.S. Appl. No. 14/139,555, 8 pages.

\* cited by examiner

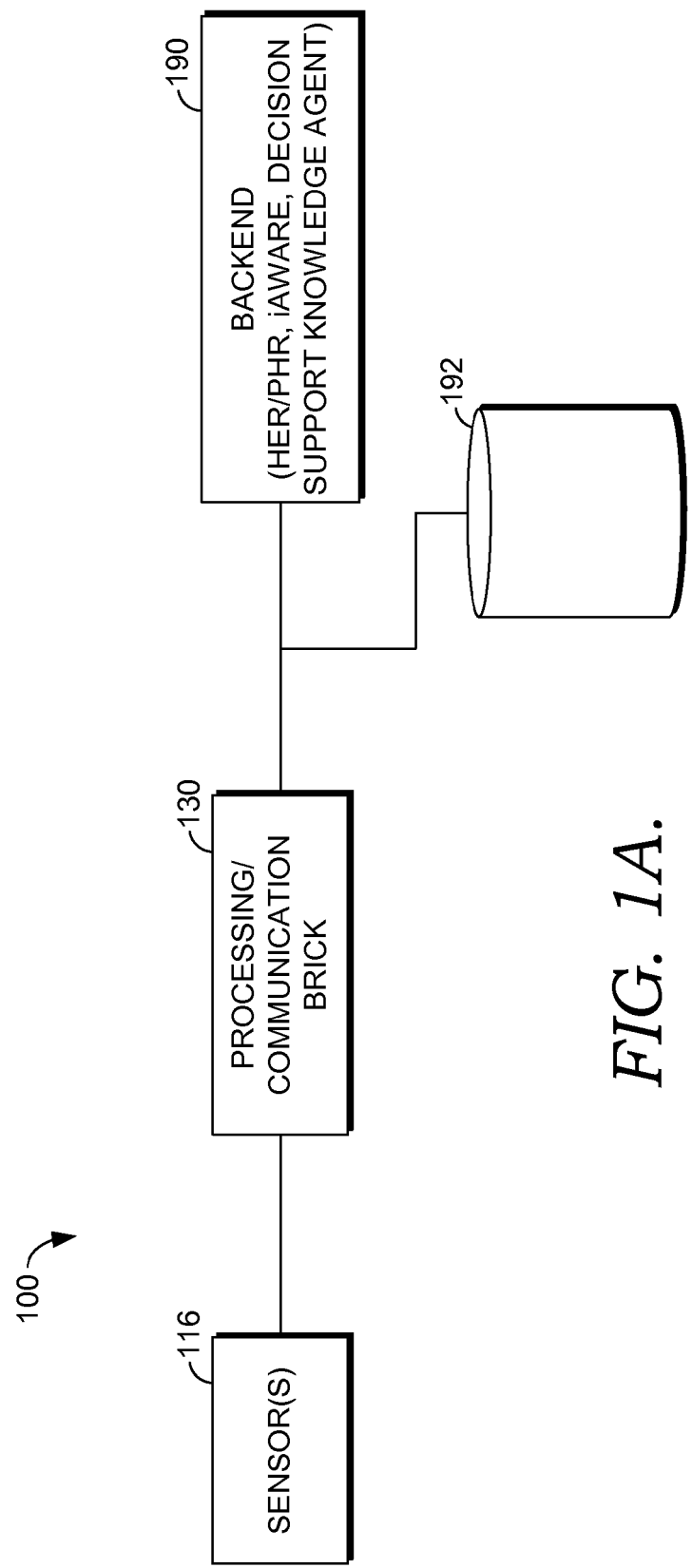

COMPUTERIZED SYSTEMS AND METHODS FOR STABILITY-THEORETIC PREDICTION AND PREVENTION OF SUDDEN CARDIAC DEATH

CROSS-REFERENCE TO RELATED APPLICATIONS

This application claims the benefit of priority of U.S. Provisional Application No. 61/291,657, filed Dec. 31, 2009, which is expressly incorporated by reference herein in its entirety.

BACKGROUND

Sudden cardiac death (SCD) is responsible for the death of up to 450,000 persons in the U.S. each year; similar incidences of SCD occur in other Western nations. The majority of these cases involve ventricular arrhythmias, not coronary occlusions and myocardial infarctions. SCD predominantly affects individuals in the prime of their lives, with most occurrences of life-threatening arrhythmia cases happening in the community (outside the hospital). Resuscitation is only attempted in a minority of patients, in part due to unavailability of defibrillation equipment and lack of knowledge and action by lay responders.

SCD is associated with common cardiac diseases, most notably heart failure, in which approximately 50% of patients die from fatal cardiac arrhythmias. Multiple factors in addition to reduced ejection fraction (EF) have been demonstrated to contribute to the risk for SCD after myocardial infarction. These include the presence of nonsustained ventricular tachycardia (NSVT), symptomatic heart failure (HF), and sustained monomorphic VT inducible by electrophysiologic cardiac testing.

However, fatal ventricular arrhythmias and SCD also frequently occur in young, otherwise healthy individuals without known structural heart disease. In structurally normal hearts the most common mechanism for induction and maintenance of ventricular tachycardia is abnormal automaticity. One form of abnormal automaticity, known as 'triggered arrhythmias,' is associated with aberrant release of $Ca^{+2}$ that initiates delayed after-depolarizations (DADs). DADs, which can trigger fatal ventricular arrhythmias, are abnormal depolarizations in myocardial cells that occur after repolarization of a cardiac action potential. The molecular basis for abnormal $Ca^{+2}$ release that causes DADs is, to date, incompletely understood.

In another form of abnormal automaticity in persons with an inherited, arrhythmogenic disorder known as "catecholaminergic polymorphic ventricular tachycardia", physical exertion and emotional stress induce polymorphic ventricular tachycardias that lead to SCD in the absence of detectable structural heart disease.

On the cellular level, prolonged repolarization can result in early after-depolarizations (EADs), which are also arrhythmogenic. Prediction of SCD based on increased beat-to-beat T-wave lability during catecholamine-provocation has been examined previously.

Depending on the arrhythmogenic mechanism(s) that prevail at a given time for a particular individual, specific steps to prevent SCD can be selected and taken, notably for people who are in hospital at the time when a ventricular arrhythmia occurs. However, comprehensive prevention is hampered by multiple factors. Foremost among these is the present inability to identify predictive factors for the majority of patients at risk of SCD and to do so far enough in advance of the event that assessment and prevention/treatment services can be effectively implemented. The reason why this is so is that many who are at risk of SCD have no prior evidence of cardiac disease and are therefore not currently engaged with a health care system where assessment and prevention might take place.

Furthermore, even in patients at markedly elevated risk, amiodarone and other conventional, nonspecific anti-arrhythmic drug treatments have proven largely ineffective in preventing SCD particularly for ambulatory patients when the SCD event occurs outside of a hospital. Antiarrhythmic drugs have failed to prevent SCD in healthcare venues (ambulatory or acute care) owing substantially to the lack of timely dosing and dose-range adjustment of the medication in advance of the arrhythmia event; or to poor effectiveness on account of the nonspecificity or lack of relation of the prevailing arrhythmogenic mechanism and the selected drug's mechanism of action; or to adverse effects associated with the medication selected. Notwithstanding the historical reasons for lack of effectiveness to-date, were advance warnings and timely dosing implemented, the existing medications and new ones that are now under development may have a better chance of reducing SCD rates and improving survival.

Additionally, guidelines for medical device-based preventive therapies, such as implantable cardioverter-defibrillators (ICDs) or cardiac resynchronization therapy (CRT) for patients at elevated risk, are often not followed. In the case of ICDs, the reason is partly because physicians perceive that the majority of patients who receive these expensive, invasive therapies never experience life-threatening arrhythmias that would cause the implanted device to deliver cardioversion-defibrillation discharges.

It is because of these factors that an improved predictive-preventive method and system would be valuable, and in embodiments of such methods and systems, prediction classification or decision-support alert signals emitted by the system may be provided at logistically convenient times far enough in advance of a life-threatening arrhythmia's occurrence to allow for effective preventive intervention in a majority of cases. More over, embodiments of such a method and system can be inexpensive and suitable for a much larger population who are at moderate risk of SCD. Such a system could find use as a tool not only for surveillance and triaging the general medical-surgical patients in hospitals and other acute-care venues but also for ambulatory, free-living individuals such as athletes and the general elderly population who have one or more risk-factors for SCD.

Effective SCD preventive interventions vary and optimal selection and personalized tailoring of them can depend upon the patient's context, gender, age, heart conditions such as heart failure or coronary artery disease or left ventricular hypertrophy, ejection fraction, exercise inducibility of ventricular tachycardia, comorbid illnesses, concomitant medications, electrolyte abnormalities, family history of SCD, and other factors. In the case of a previously asymptomatic ambulatory person, effective preventive interventions may include consultation with the personal physician, presentation at a nearby emergency department for diagnostic assessment and close monitoring, and, optionally, prophylaxis with amiodarone or ranolazine loading or, in some situations, azimilide, dofetilide, or sotalol. In the case of a person with existing, known cardiac conditions, effective preventive interventions may include admission to hospital for observation and cardiac electrophysiology exams, provision of external pacing and resuscitation equipment at the ready, consideration for implantation of an ICD, or other alternatives.

Conventional cardiac rhythm measurements, such as R-R dispersion or abnormal QTc or QT dispersion (QTd), based on small samples of ECG waveforms acquired over short intervals (10 to 30 sec) have been shown to have inadequate statistical sensitivity and specificity for the purpose of predicting SCD.

When measurements rely upon apnea or disturbed respiratory patterns as the trigger or sentinel event for predicting incipient cardiac arrhythmias, the predictions are generally only relevant when the person is asleep. Additionally, the advance notice provided by disturbed respiratory pattern signals is so short (tens of seconds) as to preclude effective interventions to prevent the predicted arrhythmia or SCD occurrences.

Many prior art methods involve cumbersome, complex, expensive and/or invasive instrumentation, or require a skilled operator in attendance.

The most accurate predictive methods, such as paced electrogram fractionation analysis (PEFA), are highly invasive (involve placement of multiple catheters in the heart), are expensive, are not widely available, are only performable by subspecialty-trained cardiologists, and are only applicable to a small subset of patients who are already known to be at risk of SCD based on other attributes.

The methods involve expensive measurements, such as genomic or proteomic laboratory tests that are not widely available and that have a performance turnaround time of many hours or days before the results and prediction are available for use, such that the prediction or classification is not timely with respect to interventions aimed at preventing the predicted occurrences.

The methods are sensitive to, and may be compromised or entirely confounded by, individual variations in patient anatomy and physiology, such as cardiac axis deviation, pulmonary congestion, dyspnea, skeletal muscle signal artifact, patient movement and positioning, diurnal variations, etc.

The methods are sensitive to, and may be compromised or entirely confounded by, individual variations in operator positioning of electrodes or sensors on the patient's body or variations in the timing and method of acquiring the specimens or data that will enter into the prediction and classification.

Noninvasive electrocardiographic tools that have been approved by the U.S. Food and Drug Administration for identifying patients at risk for SCD (such as signal-averaged electrocardiogram (SAECG) and T-wave alternans (TWA) analysis) are relatively time-consuming to perform and, as such, are accessible to only a small subset of persons at-risk, mostly less healthy persons in acute-care settings, and even in this population exhibit a false-negative rate of more than 50%, in part because the interval of data capture is limited to the time of the exam.

QT interval dispersion (QTd) is still the most common and generally-available measure used to detect repolarization problems, but this too is generally only measured in a per-exam, discrete, "snapshot" fashion. While QTd is routinely measured using manual ECG methods, software algorithms to automatically perform the measurement are available, and these could be implemented in a continuous fashion instead of discrete, point-in-time snapshots. However, these prior art software algorithms suffer from the same signal-processing problems and artifacts that arise in measuring the QT interval generally. The most common alternative approach has been to devise measurements that consider the T-wave's morphology, or overall shape. For example, one approach used the width of root-mean square curves of T-waves and found much higher correlation with the repolarization dispersion than was found for QTd. Another approach compared several novel computational measures of T-wave morphology with QTd. But short-term measurement of QTd was found to be an inadequate predictor of SCD. That approach found that a measure named total cosine R-to-T T-wave morphology dispersion was useful in assessing malignant arrhythmia risk in post-myocardial infarction patients. Machine learning techniques have also been applied to various aspects of the repolarization-dispersion problem. One approach used principal component analysis (PCA) to detect repolarization abnormalities and found the method outperformed QTd for men, and exhibited predictive performance equivalent to QTd for women. Wavelet analysis, Gaussian mesa function analysis, and machine learning approaches have been used for ECG delineation, QT interval measurement, and rhythm classification. Machine learning has also been applied to predict the occurrence of drug-induced Torsades de Pointes.

But the prior art is deficient of teachings regarding examining mathematical stability properties of the measured variables. Nor has the prior art made use of continuous realtime measurements over long periods of many hours, for instance. Despite the existence of Holter monitor type ECG recording equipment for approximately 40 years, the analysis of long-timeseries Holter data is traditionally restricted to abnormal beats or rhythms, and calculation and study of RRd(t), QTd(t), and other parameters are never performed. Only small selected portions of the recorded data are subjected to detailed analysis, and the rest are typically discarded unexamined or ignored.

SUMMARY

A system, methods and computer-readable media are provided for the automatic classification of patients according to near-term risk of life-threatening ventricular arrhythmias and sudden cardiac death. Embodiments of the invention are directed to event prediction, risk stratification, and optimization of the assessment, communication, and decision-making to prevent sudden cardiac death in humans.

In embodiments, a method for automatically predicting ventricular arrhythmias in an individual that are likely to result in sudden cardiac death (SCD) is provided. The method includes the step of obtaining ECG signals representative of electrical activity of the heart of an individual. The method also includes the steps of determining, utilizing an objective function, a QT dispersion stability index (QTdSI) from the signals, and determining the difference between the index and a reference value to detect the presence of instability of QT interval dispersion or other measurements in said signals, wherein a significant difference is indicative of an increased risk of said individual of SCD. In one embodiment, the objective function comprises a timeseries calculated from serially-acquired waveform data embodying a Lyapunov exponent of one or a plurality of ECG or other physiologic variables as functions of time. In one embodiment, the method further includes providing a notification when an increased risk for SCD is determined. In some embodiments, this notification may me communicated to a health care provider and/or may be communicated to the individual by means of an audible alarm, text message, or phone call.

BRIEF DESCRIPTION OF THE DRAWINGS

The present invention is described in detail below with reference to the attached drawing figures, wherein:

FIG. 1A depicts aspects of an illustrative operating environment suitable for practicing an embodiment of the invention.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

As one skilled in the art will appreciate, embodiments of our invention may be embodied as, among other things: a method, system, or set of instructions embodied on one or more computer readable media. Accordingly, the embodiments may take the form of a hardware embodiment, a software embodiment, or an embodiment combining software and hardware. In one embodiment, the invention takes the form of a computer-program product that includes computer-usable instructions embodied on one or more computer readable media.

Computer-readable media include both volatile and nonvolatile media, removable and nonremovable media, and contemplates media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to information-delivery media, RAM, ROM, EEPROM, flash memory or other memory technology, CD-ROM, digital versatile discs (DVD), holographic media or other optical disc storage, magnetic cassettes, magnetic tape, magnetic disk storage, and other magnetic storage devices. These technologies can store data momentarily, temporarily, or permanently.

Figure 7:
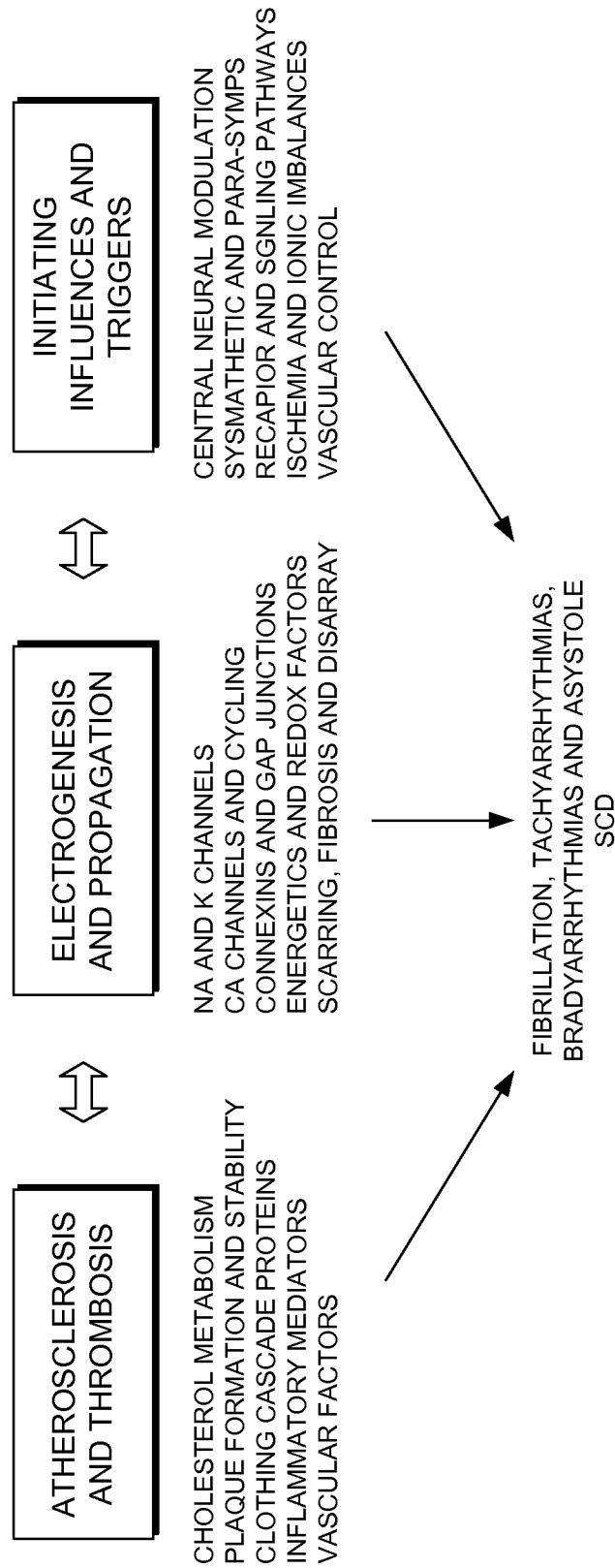
FIG. 7 illustratively depicts inter-related causative factors resulting in SCD.

Embodiments of the present invention provide a computerized system, methods, and computer-readable media for automatically identifying persons who are at risk for cardiac arrhythmias and sudden cardiac death through the use of a system, which in one embodiment, includes noninvasive, portable, wearable electronic device and sensors equipped with signal-processing software and statistical predictive algorithms that calculate stability-theoretic measures derived from the digital electrocardiogram timeseries acquired by the device. FIG. 7 illustratively depicts inter-related causative factors resulting in SCD.

The measurements and predictive algorithms embedded within the device provide for unsupervised use in the home or in general acute-care and chronic-care venues and afford a degree of robustness against variations in individual anatomy and sensor placement. In embodiments, the present invention provides a leading indicator of near-term future abnormalities, proactively alerting the user (for example, 2 hours or more in advance, in one embodiment) and providing the wearer and/or care providers with sufficient advance notice to enable effective preventive maneuvers to be undertaken. In one exemplary embodiment, the device is equipped with radiofrequency telecommunication capabilities that enable integration with case-management software, electronic health record decision-support systems, and consumer personal health record systems.

By way of example and not limitation, a user using an embodiment of the invention may be able to go about his or her daily routine but be provided an advanced warning of any abnormalities such as a detonation or improvement of the user's condition or an increased likelihood of an event such as SCD, COPD, asthma, TIA, stroke, or other conditions, for example. In one embodiment, the user may don one or more sensors, which could be a chest-strap sensor, a badge sensor attached to or integrated into the user's clothing, a watch-sensor or other sensor in approximate contact with the user and that is wirelessly communicatively-coupled to a smart phone located on or near the user's body. In this exemplary embodiment, the smart-phone may include an app which when executed receives user data from the sensors, calculates the stability-theoretic measures, and communicates the results with the user, the user's health care provider, case-management software, decision-support systems, or personal health record systems. For example, the phone may notify the user in advance, via an alarm or vibration, and may also notify a family member, the user's health care provider, electronic-health record decision-support systems or personal health record systems, via a call, email, http, sms text-message, or other form of radiofrequency communication, that the user has an increased likelihood of a near-term future abnormality. This enables the user or care providers to take preventative measures.

An exemplary operating environment for the present invention is described in connection to FIGS. 1A, 1B and 2, and relates generally to the description of a mobile wearable system for stability-theoretic prediction and prevention of events such as SCD, for use in some embodiments of the invention, and described below in connection to FIGS. 1A, 1B and 2. Referring to the drawings in general, and initially to FIG. 1A in particular, an exemplary operating environment 100 is provided suitable for practicing an embodiment of our invention. We show certain items in block-diagram form more for being able to reference something consistent with the nature of a patent than to imply that a certain component is or is not part of a certain device. Similarly, although some items are depicted in the singular form, plural items are contemplated as well (e.g., what is shown as one data store might really be multiple data-stores distributed across multiple locations). But showing every variation of each item might obscure the invention. Thus for readability, we show and reference items in the singular (while fully contemplating, where applicable, the plural).

As shown in FIG. 1A, environment 100 includes one or more sensors 116. In one embodiment, sensors 116 include one or more transducers or types of sensors operable for providing electrical signals corresponding to measurements of various conditions or states of a user. Embodiments of sensor 116 may further include a power supply, processor, memory operable for acquiring and storing user-information and programming instructions, and communication component for communicating the resulting measurements of user-information with brick 130. In some embodiments, the transducer may be a standard electrode, such as a single-terminal electrode, or a specialized multi-segment or noise-reduction electrode.

In some embodiments one or more specialized noise-reduction electrodes may be integrated on a wearable fabric elastomeric band positioned on the user, such as around the user's chest, thereby eliminating or reducing noise, interference, distortion, or artifacts and also improving ease-of-use and patient compliance. In some embodiments, the processor of sensor 116 is operable to control the frequency of measurements; for example, to read a transducer's output at certain intervals such as 50 times each second; to pre-process or condition the signal, including applying a threshold, noise-filter, or normalizing the raw user-derived signal; read from or store the user-information in memory, and communicate the acquired timeseries of user-information with brick 130 via a communication component of sensor 116.

Embodiments of sensor 116 may be designed to measure one or more conditions or states of a user. For example, in one embodiment sensor 116 obtains electrical cardiac signals of a user and may be worn as a chest-strap. Such a sensor may be designed to measure electrical signals associated with the nerves of the heart or the heart muscle or both. In another embodiment, sensor 116 may include an optical transducer for measuring chemicals in the skin such as keytones, which may be used for determining ketoacidosis of the user. Such an embodiment of sensor 116 may be configured as a skin patch, arm- or leg-band, on the back of a watch, or ankle band, for example. Another embodiment of sensor 116 includes one or more optical sensors for detecting an optical signal across the skin to look at carbox-symmetry, $CO_2$ levels, $O_2$ levels, or a combination of these levels.

In some embodiments, these levels are measured at 10 to 50 times a second thereby resulting in a timeseries of user-information that maybe communicated to brick 130. Other embodiments of sensors 116 include sensors for measuring blood pressure, heart rate, temperature, chemicals such as chemicals in the blood, breath, or on the user's skin, skin or tissue properties, oxygen levels, user motion, movement, or position, or other variables associated with the user's condition or state. Such sensors are configured to be positioned on or near the user's body in an appropriate manner so that they may function to sense user-data. For example, heart-related sensors may be positioned on or near the chest or at other appropriate locations on the user's body.

In some embodiments, sensor 116 may be worn in contact with user, worn on user's clothes, or located in a user's seat, bed, toilet, or elsewhere in the user's environment, depending on specific type of user-information that the sensor is intended to measure. In one embodiment, sensors 116 include one or more accelerometers, gyroscopic meters, or combination of such devices as to enable one or more sensors 116 to detect user motion, user position or orientation, and sudden changes in user position. In one embodiment, such a sensor 116 may be optimally positioned on the user to measure motion and orientation, such as inline with the user's spine. In one embodiment, the accelerometer and gyroscopic chip-sets built into many smart phones may be used as sensor 116. In such an embodiment, the smart phone, running a program for determining stability-theoretic measures, may monitor user motion-stability and provide to the user and health-care provider early earning warning of a likelihood of increased risk for falling.

In some embodiments, multiple sensors 116 may be employed on or about the user. For example, it may be desirable to have more than one sensor for measuring certain user information such as ketones in the skin, for example, as circulation on certain users varies in the user's body. Additionally, one or more sensors may become compromised, and having multiple sensors provides for robustness. For example a watch sensor may get wet when the user washes his hands and fail to operate as normal, while a second sensor located on the user's ankle may remain effective. It is also contemplated that multiple sensors of different sensor-types may be utilized to provide a combination of user-information that may more accurately identify a condition or state of the user or increased likelihood of a particular event occurring. For example, a user suffering from the early conditions of a stroke may exhibit multiple signs detectible by different types of sensors 116, such as motion sensors 116, blood-pressure sensors 116, and skin-chemical sensors 116.

Figure 1B:
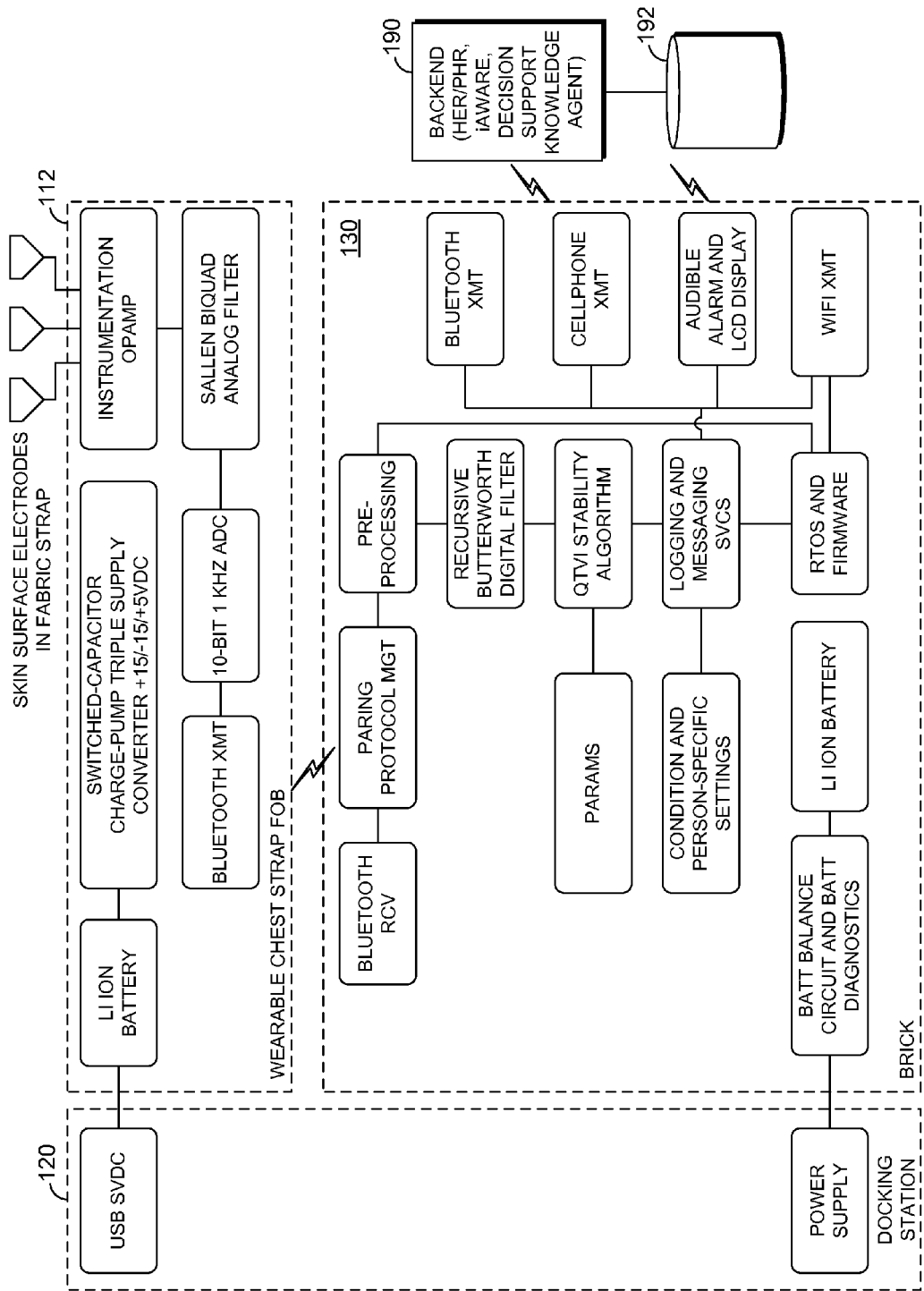
FIG. 1B depicts aspects of an illustrative operating environment suitable for practicing an embodiment of the invention.

Continuing with FIG. 1A, environment 100 includes processing/communication brick 130. Exemplary embodiments of brick 130 are discussed in greater detail in connection to FIG. 1B, but some embodiments of brick 130 include one or more processors operable for processing user-sensor information and determining stability-theoretic measures, a communication module for receiving information from the user-sensors and for communicating results to the user or health-care provider, and a memory for storing received user-information, determined results, and programming instructions. Brick 130 may worn on the user's body, such as clipped to a belt, in a holster, or around the user's neck, or can be carried by the user, such as in the user's pocket or purse, or may be kept with a close enough proximity to the user as to communicate with sensor(s) 116. In some embodiments, sensor(s) 116 are housed within or on brick 130.

In some embodiments, brick 130 is a smart phone running one or more application programs or "apps" for receiving user-sensor information, determining stability-theoretic measures, and communicating results to the user and health care provider. In a smart-phone embodiment, brick 130 uses the phone's communication equipment for communicating user information to a backend, such as a health care provider or decision-support knowledge agent. Brick 130 may use other communication features of the smart phone such as Bluetooth or Wi-Fi to communicate with one or more sensors 116 and in some embodiments, a base station or user computer.

A smart phone may be communicatively-coupled with an additional component for facilitating communication with one or more sensors 116, for processing user-information, or for storing and communicating user results. For example, in one embodiment, brick 130 is communicatively-coupled to a holster or other component containing a communication module for communicating with one or more sensors 116. Such an embodiment is useful where sensors 116 use a communication protocol that is not compatible with brick 130. For example, where sensors communicate using Bluetooth, but brick 130 is embodied on non-Bluetooth enabled smart phone, the user may attach a Bluetooth module to the smart phone to enable it to communicate with sensors 116. Similarly, where sensors 116 communicate using ZigBee or another low-rate wireless personal area network platform, a user may couple a ZigBee-enabled communication module to their smart phone. In another example embodiment, a smart phone may be communicatively-coupled with a base station (not shown) located in the user's house. In one embodiment, the base station could be a personal computer connected to a wireless router or a laptop equipped with RF communication capability such as Wi-Fi or Bluetooth. In one embodiment, the base station communicates with backend 190.

In another embodiment, brick 130 communicates directly with backend 190. Backend 190 includes the health care provider computer system and devices, case-management software, electronic health record decision-support systems and devices, or consumer personal health record systems and devices. In some embodiments, brick 130 stores information on data store 192, which may be local or remotely located, and which may be accessible by backend 190, in some embodiments. In some embodiments, data stores 192 comprises networked storage or distributed storage including storage on servers located in the cloud. Thus, it is contemplated that for some embodiments, the information stored in data store 192 is not stored in the same physical location. For example, in one embodiment, one part of data store 110 includes one or more USB thumb drives or similar portable data storage media. Additionally, information stored in data store 192 can be searched, queried, analyzed via backend 190, such as by a health care provider or by a decision-support knowledge agent, for example.

In some embodiments, sensors 116 communicate with other sensors 116 and with brick 130 over a wired or wireless communication protocol. In one embodiment, sensors 116 communicate using Bluetooth, Wi-Fi, or Zigbee protocols. In some embodiments a low-powered communication protocol is desirable in order to preserve the batter life of the sensor 116. In some embodiments using a communication protocol having a narrow bandwidth, such as Zigbee, sensors 116 may also include a memory buffer for storing user-derived information until it is communicated to brick 130. Sensors 116 may also communicate with other sensors 116 or directly with a base station, in some embodiments.

Turning now to FIG. 1B, an exemplary operating environment suitable for practicing an embodiment of the invention is shown and referenced generally as 150. As shown in FIG. 1B, brick 130 is communicatively coupled to wearable chest strap sensor 112, which is one embodiment of sensor 116, and docking station 120. In the embodiment shown in FIG. 1B, docking station 120 recharges a battery in brick 130 and in chest-strap sensor 112. Brick 130 is also communicatively coupled to backend 190, and data store 192, which are described previously in connection to FIG. 1A.

The embodiment illustratively depicted in FIG. 1B, may be used for generating a Lyapunov exponent classifier and verifying and validating whether such a detector achieves statistical sensitivity and specificity in the intended mortality range of deployment, sufficient for satisfactory performance in the use for classifying patients according to in-hospital mortality outcome.

In the embodiment shown in FIG. 1B, chest-strap sensor 112 includes one or more skin surface electrodes in the fabric of the chest strap. In this embodiment, the electrodes are coupled to an instrumentation operational amplifier, an analog filter, an analog-to-digital converter, and a Bluetooth or similar RF communication component, thereby enabling chest strap sensor 112, when positioned on the user's chest, to obtain raw electrocardiogram signals of the user's heart, capture and digitize the raw ECG signals, and communicate this information to brick 130. Chest-strap sensor 112 also includes a power supply made up of a battery and multiple-output supply converter.

In the embodiment shown in FIG. 1B, brick 130 includes a Bluetooth or similar RF communication component operable to receive user-information from chest-strap sensor 112 or from other sensors 116, preprocessing and filtering components operable to condition and format the received user information for the QT variability index (QTVI) stability processing, and one or more processors for determining QTdSI, which is described in connection to FIGS. 3 and 4, below. Embodiments of brick 130 may also include a Bluetooth, cell-phone, or Wi-Fi communication component for communicating results ultimately to backend 190 and data store 192, and an alarm and display for providing results, diagnostic feedback, power levels, and other information to a user or for receiving inputs from a user such as parameters and device settings. Embodiments of brick 130 may also include memory for storing parameters, settings, firmware and programming instructions, and determined results. Embodiments of brick 130 may also include a power supply which in one embodiment comprises a battery and a battery balance circuit. In one embodiment, brick 130 is a computer system with one or more processors, memory, and input/output functionality.

In one embodiment, brick 130 is a computer system comprising the following hardware and firmware components: a 32-bit 48 MHz AT91SAM7S256 (ARM7TDMI) main microprocessor with 256 KB flash memory and 64 KB RAM, an 8-bit 4 MHz ATmega48 microcontroller with 4 KB flash memory and 512 Bytes RAM, a 26 MHz CSR BlueCore 4 Bluetooth controller with 1 MB flash memory and 47 KB RAM, and 100×64 pixel LCD matrix display. In one embodiment, ECG pre-processing, recursive IIR low-pass Bessel filter, and QTdSI calculation software algorithms were implemented in a dialect of the C language (NXC) using the BricxCC compiler and version 1.28 firmware for the ARM7 processor. It should be understood that variations in hardware and firmware are contemplated by and within the scope of the invention, and are provide here for illustrative purposes.

Figure 2:
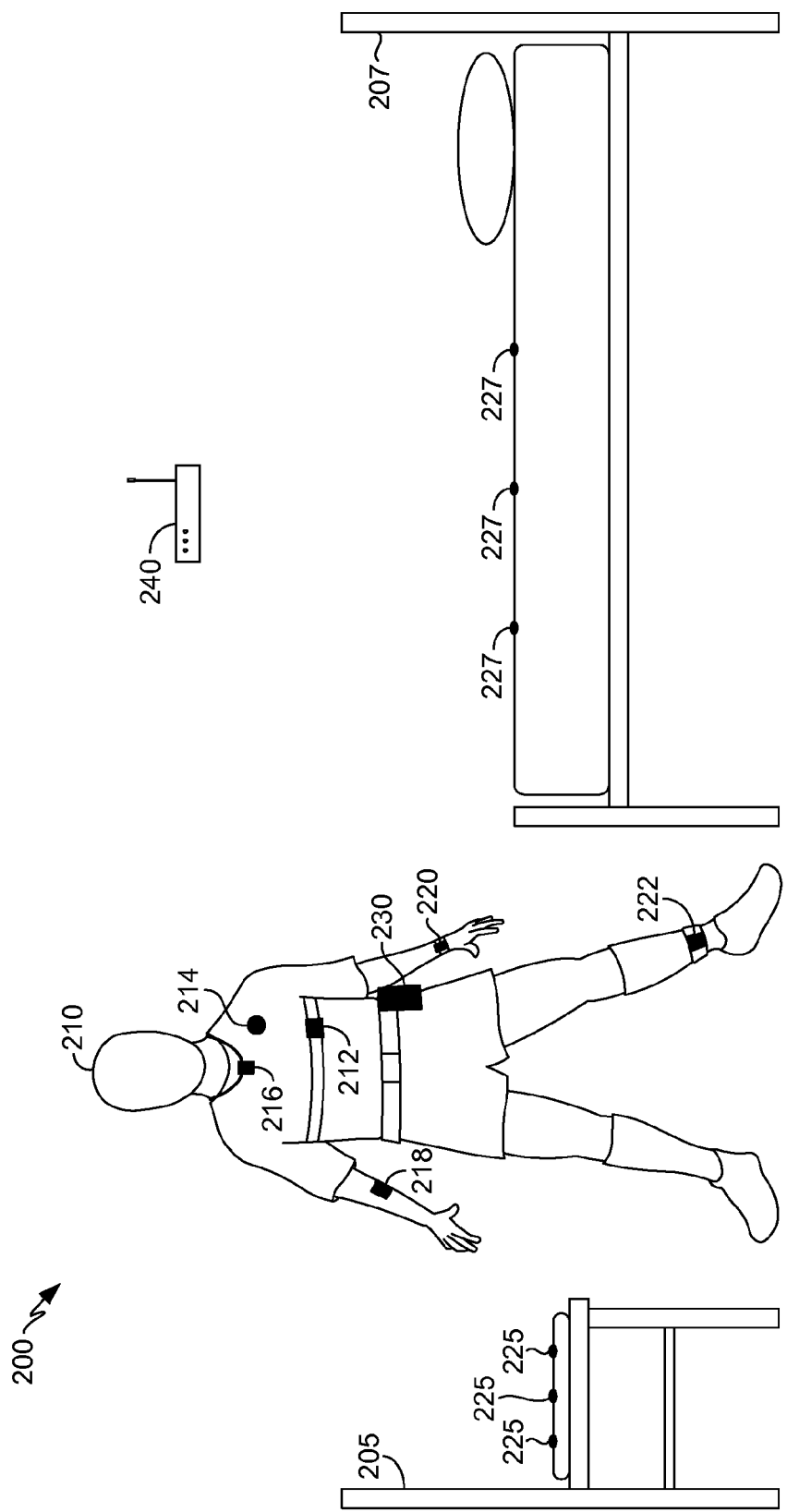
FIG. 2 depicts aspects of an illustrative operating environment suitable for practicing an embodiment of the invention.

FIG. 2 illustratively depicts aspects of an illustrative operating environment suitable for practicing embodiments of the invention and is referenced generally as 200. Environment 200 depicts a user 210 wearing various example types of sensors 116, including: chest-strap sensor 212, badge-sensor 214, which may be attached to a user's clothing or integrated into a user's clothing, necklace sensor 216, skin-patch sensor 218, watch-strap sensor 220, and ankle or leg sensor 222. User 210 is also wearing a brick 230 at the user's waist. Also depicted in environment 200 is a chair 205 having sensors 116 integrated into a seat cushion, shown as sensors 225, and a bed 207 having sensors 116 integrated into the bed shown as sensors 227. In some embodiments, environment 200 includes a base station 240, which may be communicatively coupled to brick 230 or one or more sensors 116. As further described in connection to FIG. 1A, in some embodiments, a base station, such as base station 240, is communicatively coupled to a user's computer, to a backend 190, or to data store 192.

Figure 5:
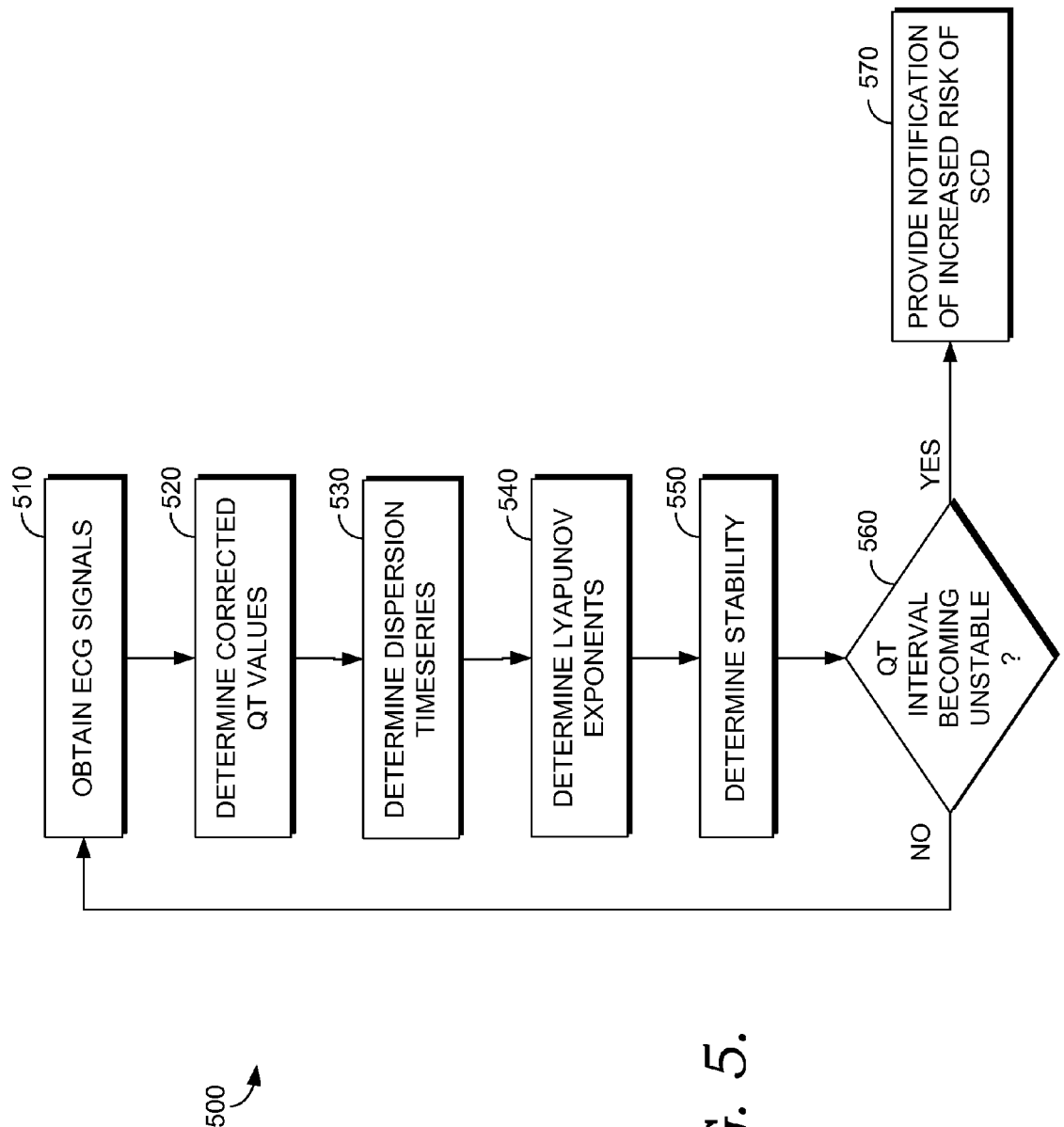
FIG. 5 depicts a flow diagram of an exemplary method for determining a QT dispersion stability index for an individual, in accordance with embodiments of the invention.

Turning now to FIG. 5, a flow diagram 500 is provided illustrating an exemplary method according to one embodiment. At a high level, flow diagram 500 illustratively depicts a method for determining a QT dispersion stability index (QTdSI) for an individual. An example of the QT interval is illustratively provided in FIG. 6. The QTdSI is determined by applying an objective function to user-derived information such as ECG signal information obtained from one or more sensors 116. Some embodiments of the invention process the information in serial heartbeats in the individual's electrical cardiac signals to calculate QTdSI(t) timeseries, where t represents time, as a function of the individual's instantaneous QTdSI determinations. As shown in flow diagram 500, a logistic regression equation and algorithm based on Lyapunov stability measures of QT dispersion as a continuous or discrete function of time is utilized. A Lyapunov exponent (of QTdSI(t) or any other timeseries signal) is a quantitative measure of separation of trajectories that diverge widely from their initial positions and is related to how chaotic a system is. The larger the exponent, the more chaotic the system. For periodic signals, the Lyapunov exponent is zero. A random but stable signal will also have an exponent very close to zero.

In another embodiment, a decision tree algorithm may be used to evaluate the classification ability of several methods of measuring repolarization dispersion. In yet another embodiment, a support vector machine (SVM) algorithm utilizing timeseries of calculated ECG variables including width of root-mean-square (RMS) T-wave, total cosine T-wave dispersion, T-wave loop dispersion, normalized T-wave loop area, and relative T-wave residuum is applied to generate a prediction of SCD risk. Still in yet another embodiment, a combination of a Lyapunov-based algorithm, a decision tree algorithm, or a support vector machine may be utilized.

At a step 510, electrocardiogram (ECG) signals of a user are obtained using one or more sensors 116. User-information representative of the ECG signals is communicated from one or more sensors 116 to brick 130. In one embodiment, the obtained ECG-signal information includes one or more QT intervals. An example QT interval is illustratively provided in FIG. 6. In one embodiment, sensor 116 captures QT waveforms corresponding to the user's heart beats, thereby resulting in a timeseries of QT intervals. It will be understood by those skilled in the art that in some embodiments, other ECG waveform measures or physiologic timeseries may be used without departing from the scope of the invention. For example, in some embodiments timeseries variables relating to respiratory, glucometry, accelerometry, oximetry, capnometry, plethysmography (perfusion), or other physiologic variables may be used.

Figure 6:
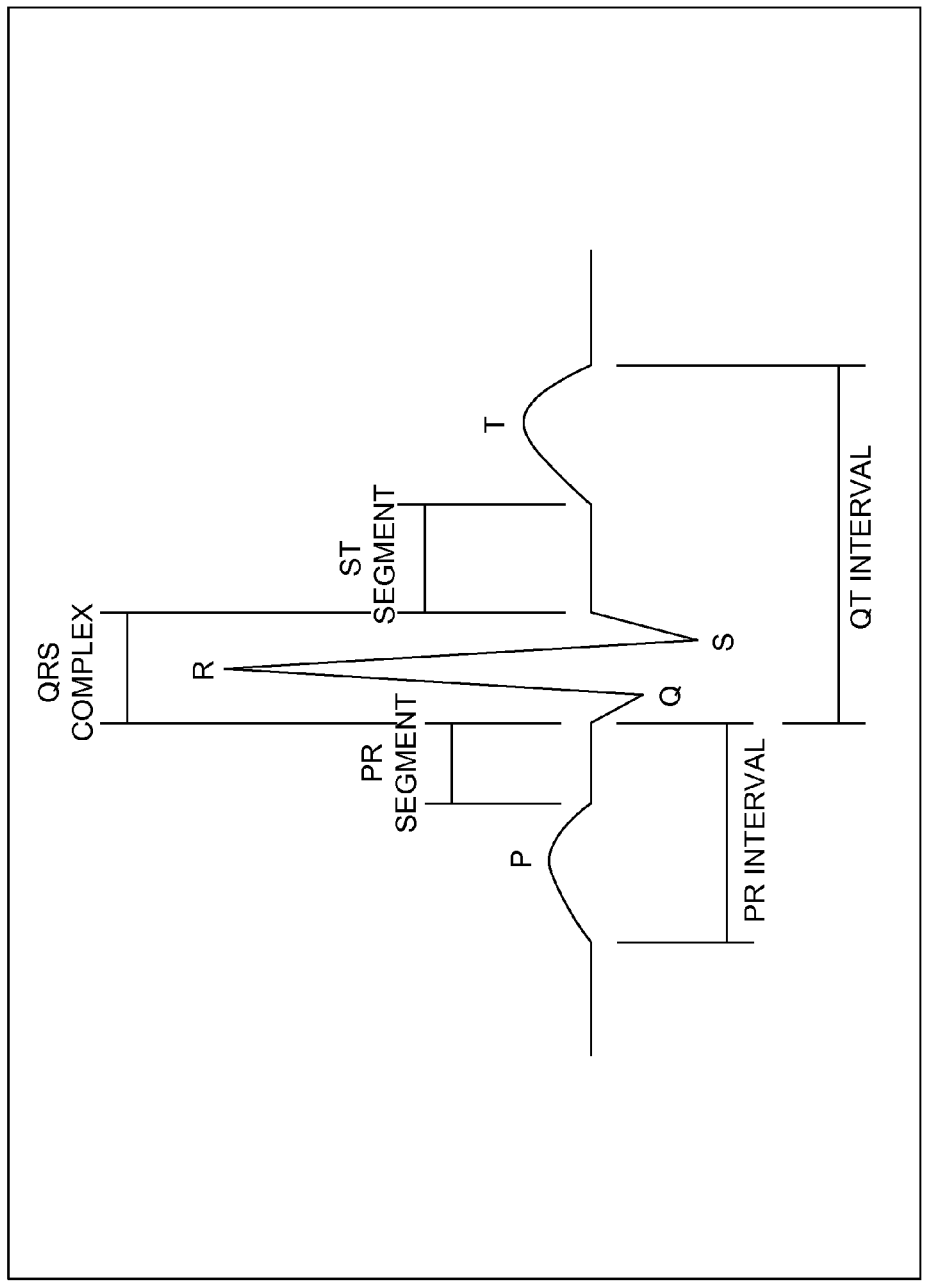
FIG. 6 depicts an exemplary EKG signal of normal morphology identifying the P, Q, R, S, and T segments of the waveform.

In steps 520 through 550, the QTdSI as a function of the continuous or discrete QT interval timeseries is calculated. In some embodiments, any ectopic beats and the sinus beats immediately preceding and following the ectopic beats are first eliminated, as part of a step 520 before calculating the maximal value of root-mean-square differences for isochronic points of the repolarization interval between pairs of consecutive beats. Low-pass filtering may be performed to remove baseline drift from the electrical signal, in some embodiments. Normalizing the maximal value of root-mean-square differences to the absolute magnitude of the signal-averaged QRS complex may also be performed, in some embodiments, before calculating and updating the QTdSI(t) timeseries. FIG. 6 depicts an illustrative example of the QRS complex. Instructions carried on a computer-readable storage medium (e.g., for identifying QT intervals and calculating QTdSI(t)) can be implemented in a high level procedural or object oriented programming language to communicate with a computer system, in one embodiment. Alternatively in another embodiment, such instructions can be implemented in assembly or machine language. The language further can be compiled or interpreted language, in one embodiment.

It is further contemplated that in some embodiments, the QTdSI-related processing occurring in steps 520 through 540 occurs in realtime or near realtime, simultaneously, as user-information is collected in step 510, thereby allowing a skilled operator to monitor an individual's QTdSI during pharmacologic or exercise physiologic stress, if desired. More generally, in some embodiments, processing steps 520 through 550 are performed substantially simultaneously with the step 510 of collecting the cardiac signals in near real-time, so as to enable the ambulatory consumer to go about their daily activities and receive smartphone or other mobile alert messages from brick 130 device in case any elevated-risk conditions are detected.

At step 520, a corrected QT value is determined. This determination may be performed by processing in sensor 116, in brick 130 or both. In embodiments, artifact censoring and a noise filter or other DSP filtering may be applied to the raw signal information. In some embodiments, the raw QT value is then normalized thereby resulting in a corrected QT value. In one embodiment the raw QT value is normalized to what it would be if the heart rate was 60.

At steps 530, 540, and 550, QTdSI timeseries is determined, Lyapunov exponents are calculated, and used to determine stability of the monitored condition of the user. By way of example and not limitation, the methodology of the invention may be understood through the following steps: Let $L(x_1, x_2, \ldots, x_n)$ be a scalar function of n components of x, where the n components (sampled time-points of the QT dispersion timeseries QTd) comprise the vector $x=\{x_1, \ldots x_n\}$. $L(x)$ is positive-definite in a neighborhood N of the origin if $L(x)>0$ for all $x \neq 0$ in N and $L(0)=0$. Let $x^*(t)=0$, $t \geq t_0$ be the zero solution of the homogeneous system $x\phi=Ax$ where $x(0)=x_0=0$. Then $x^*(t)$ is globally stable for $t \geq t_0$ if there exists $L(x)$ with the following properties in some neighborhood N of 0: (i) $L(x)$ and its partial derivatives are continuous; (ii) $L(x)$ is positive-definite, or $L(x)>0$; and (iii) $dL(x)/dt$ is negative-definite, or $dL(x)/dt<0$.

By (ii) the quadratic form $L(x)$ exhibits an ellipsoid curve. By (iii), the ellipsoid curve shrinks to zero. Choose $\epsilon>0$ such that $N\epsilon \subset N$ above. Any half-path starting in $N\epsilon$ remains in it because $L(x)$ is a quadratic form (by (ii)) which exhibits an ellipsoid curve that is continuous as well as its partial derivatives (by (i)). The same holds for every sufficiently small $\epsilon>0$ and hence for every sufficiently small neighborhood of the origin. The zero solution is therefore globally stable.

In other words, the system $(dx/dt)=Ax$ is globally stable if and only if for some positive-definite matrix W, the equation: $A^t H+HA=-W$ has a positive-definite matrix H. If for some positive-definite matrix W, the equation $A^t H+HA=-W$ has a positive-definite matrix H, let us show that $(dx/dt)=Ax$ is globally stable. Since H is positive-definite, then $L(x)=x^t Hx$ is positive-definite (where $x^t$ is now the transpose of x and not the time derivative), i.e. $L(x)>0$. Also, L(x) positive-definite implies that V(x) and its partial derivatives are continuous. Differentiating L(x), then: $dL(x)/dt = (dx^t/dt)Hx + x^t H(dx/dt)$ or, as $dx/dt = Ax$: $dL(x)/dt = (Ax)^t Hx + x^t HAx = x^t A^t Hx + x^t HAx = x^t(A^t H + HA) x$. Thus, as $A^t H + HA = -W$: $dL(x)/dt = x^t(-W)x$. W determined to be positive-definite implies that $-W$ is negative-definite, thus: $dL(x)/dt = x^t(-W)x < 0$.

Finally, it is notable that (i) L(x) and its partial derivatives are continuous; (ii) V(x) is positive-definite; (iii) $dL(x)/dt$ is negative-definite. As a result, $dx/dt$ is globally stable according to our previous theorem. Conversely, if $dx/dt = Ax$ is stable, then for some positive-definite matrix W, the equation $A^t H + HA = -W$ has a positive-definite matrix H. $dx/dt = Ax$ stable implies all the eigenvalues of A are negative, i.e. $\lambda < 0$ for any eigenvalue $\lambda$ of A. Now, as $\lambda x = Ax$, then $(Ax)^t = (\lambda x)^t$, which implies $x^t A^t = \lambda x^t$. Thus, premultiplying $A^t H + AH$ by $x^t$ and post-multiplying it by x, the following is obtained: $x^t(A^t H + HA)x = x^t(-W)x$; or: $x^t A^t Hx + x^t HAx = x^t(-W)x$; or substituting in $\lambda x^t$ and $\lambda x$: $\lambda x^t Hx + x^t H\lambda x = x^t(-W)x$; or simply: $2\lambda x^t Hx = x^t(-W)x$. As $-W$ is negative-definite, then $x^t(-W)x < 0$, thus $2\lambda x^t Hx < 0$. As $\lambda < 0$ by the assumption of stability, then it must be that $x^t Hx > 0$, or H is a positive-definite matrix. Accordingly, a real n×n matrix A is a stable matrix if and only if there exists a symmetric positive-definite matrix H such that $A^t H + HA$ is negative-definite. In one embodiment, a choice of $W = I$ may be made and H can be solved and solve for H in the equation $A^t H + HA = -I$. The solution has the form $H = \alpha(A^t)^{-1}A^{-1} + \beta I$ where $\alpha$ and $\beta$ are constants. Thus, choosing a Lyapunov function, $L(x) = x^t Hx$, this solution is used to determine H. The Lyapunov function or thread may be executed continuously, under a real-time operating system (RTOS), in some embodiments, enabling parameters and timeseries information to be passed to the Lyapunov function or thread in near realtime.

Furthermore, in some embodiments, a second-order polynomial function $f(x) = r \ast x \ast (1-x)$ is utilized to represent a system whose stability may be characterized by the invention. In one embodiment, the system may be characterized by a function of different order or form. If the structure of a particular system is not known, the structure may be developed by Taylor series regression, spectral analysis or time-series analysis techniques or other methods of modeling known to those of skill in the art.

At a step 530 a dispersion time series is calculated. In one embodiment, a standard deviation (SD) is calculated on an M-wide time series array, such as, for example, $SD\{QT_1, \ldots, QT_{N-M}\}$, $SD\{QT_2, \ldots, QT_{N-M+1}\}$, ..., $SD\{QT_{M+1}, \ldots, QT_N\}$. In one embodiment M may vary between 1000 to 10,000 samples; with accuracy generally increasing as the size of M increases.

At a step 540, Lyapunov exponents are calculated for each member of the time series, thus: $SD\{QT_1, \ldots, QT_{N-M}\} \to \lambda_1$, $SD\{QT_2, \ldots, QT_{N-M+1}\} \to \lambda_2$, ..., $SD\{QT_{M+1}, \ldots, QT_N\} \to \lambda_{M+1}$. At a step 550, stability is assessed based on the determined values of the Lyapunov exponents. In some embodiments $\lambda_i > 0$ implies an unstable process. In some embodiments, a threshold TH may be applied. For example, for instability to be present, $\lambda_i > TH$, which can account for minor fluctuations that may occur in the user, such as fluctuations that may arise when a user's activity level and heart rate change. In other embodiments, such as in the example discussed later on, the difference between $\lambda_i$ and a reference value is determined, and instability is present where this difference exceeds a certain threshold.

At a step 560 it is determined whether the user's QT interval is showing signs of instability, based on the results of step 550. In one embodiment, if the stability is present, then the process returns to step 510 and additional ECG signals or other physiologic timeseries information is obtained from one or more sensors 116. In one embodiment, new QT-interval information or other physiologic timeseries information continuously collected as it is available simultaneously as processing for determining stability-theoretic measures occurs. In one embodiment, the Lyapunov exponents are calculated on a sliding boxcar array that is M-samples wide, with new Lyapunov exponents calculated each W samples. In embodiments where W equals 1 heart beat, then new Lyapunov exponents are calculated on the M-wide timeseries array for each new heart beat. In some embodiments, W may represent approximately 400 samples, thus for example at 60 BPM, Lyapunov exponents would be calculated on the M-wide array every 400/60 minutes. If at step 560, the results of step 550 indicate the presence of instability, then the method proceeds to step 570. At a step 570, a user, health care provider, or decision support system is notified that the user is becoming unstable. In one embodiment, this instability indicates that the user is facing an increased likelihood of SCD or other cardiac abnormality. In one embodiment, this instability indicates a change in the patient's condition, which may be for the better or worse. In one embodiment, the user may be notified via brick 130 in the form of a text message, audible alarm or vibration. In one embodiment, the health care provider maybe notified via brick 130 in the form of a text message, call, or other appropriate form of communication. In one embodiment, a visual or graphical display of the electrical signals or a numerical or digitized representation of the monitored ECG variables and stability indices may be presented on brick 130, a user's computer communicatively coupled to brick 130, or a health care provider's computer communicatively coupled to backend 190. For example, in one embodiment, an audible alert sounds or a vibration is emitted upon detection of patterns and QTdSI values indicative of actionable increased risk of SCD. In one embodiment, a radiofrequency message may be emitted to security-/confidentiality-controlled, mated transceivers such as BlueTooth smartphones, Wi-Fi connections with personal computers or electronic medical records systems, and similar devices.

Figure 3:
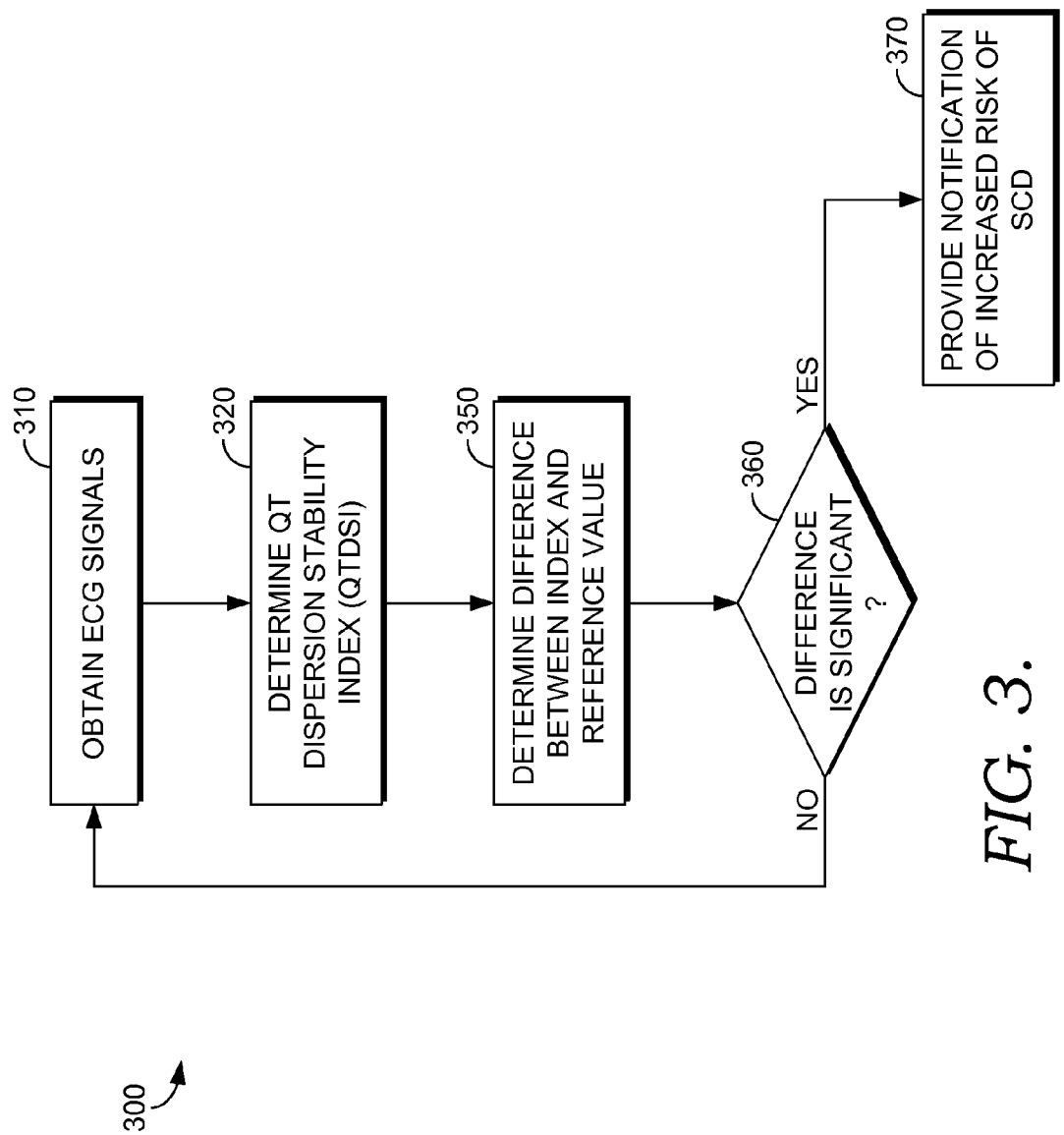
FIG. 3 depicts a flow diagram of an exemplary method for automatically predicting ventricular arrhythmias in an individual that are likely to result in sudden cardiac death, in accordance with embodiments of the invention.

Turning to FIG. 3 a flow diagram 300 is provided illustrating an exemplary method according to one embodiment. At a high level, flow diagram 300 illustratively depicts a method for determining a QT dispersion stability index (QTdSI) for an individual. The QTdSI is determined by applying an objective function to user-derived information such as ECG signal information obtained from one or more sensors 116. The method also includes determining the difference between the stability index value and a reference value to detect presence of instability of QT interval dispersion or other measurements. It has been determined, as further described below in connection to that a significant difference between the two values indicates an increased risk of Sudden Cardiac Death (SCD) for an individual. In one embodiment, the reference value is selected based on other parameters associated with the user.

At a step 310, electrocardiogram (ECG) signals of a user are obtained using one or more sensors 116. User-information representative of the ECG signals is communicated from one or more sensors 116 to brick 130. In some embodiments, pre-processing and conditioning of the ECG signal information, which may include, for example, artifact censoring, normalization, or DSP filtering, as described in connection with step 520 in FIG. 5, takes place either at the sensor 116 in brick 130, or both. At a step 320, QTdSI is determined in accordance with the method described in connection to steps 520 to 550 of FIG. 5. At a step 350, the difference between the QT dispersion stability index and a reference value is determined. Based on the results of this difference, at a step 360, a determination is made as to whether the difference is significant.

In one embodiment, significance is based on parameters associated with the particular user. For example, a younger more active user without a known condition may be afforded a greater difference than a user who has a known history of cardiac arrhythmias or otherwise has a higher risk for SCD. At step 360, where the determined difference is not significant, the method returns to step 310. In one embodiment, new QT-interval information or other physiologic timeseries information is continuously collected as it is available simultaneously as processing for determining stability-theoretic measures occurs, as described above in connection to FIG. 5. At step 360, where the determined difference is significant, the method proceeds to a step 370. At step 370, notification of increased risk for SCD is provided. In one embodiment, the notification is provided in a manner as described at step 570 in connection to FIG. 5.

Figure 4:
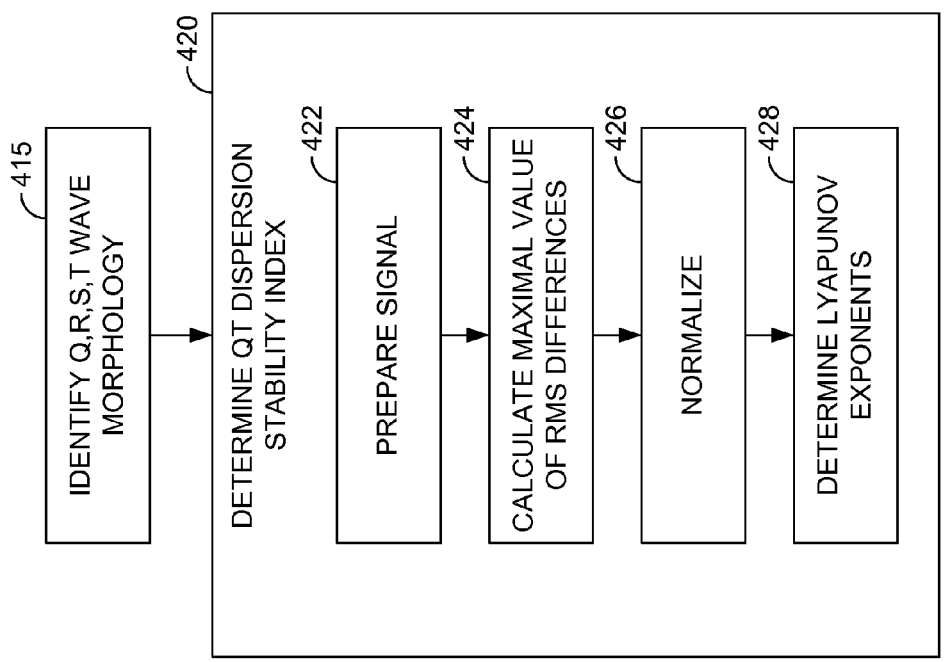
FIG. 4 depicts a flow diagram of an exemplary method for determining a QT dispersion stability index for an individual, in accordance with embodiments of the invention.

Turning now to FIG. 4, a flow diagram 400 is provided illustrating an exemplary method according to one embodiment. At a high level, flow diagram 400 illustratively depicts a method for determining a QT dispersion stability index (QTdSI) for an individual. With reference to FIG. 6, at a step 415 of FIG. 4, Q, R, S, and T wave morphology is determined for isochronic points between substantially-consecutive T waves in signals representative of electrical activity of the heart of the individual. At a step 420 the QTdSI is computed, in accordance with the method described in connection to steps 520 to 550 of FIG. 5, as a function of the morphology determined in step 415. In the embodiment shown in FIG. 4, at a step 422, the user-derived signal is prepared. In some embodiments, this includes pre-processing and conditioning of the ECG signal information, which may include, for example, artifact censoring, normalization, or DSP filtering, as described in connection with step 520 in FIG. 5. Such preprocessing may be performed by sensor 116, brick 130, or both, in some embodiments. At a step 424, the maximal value of root-mean-square differences for isochronic points of a repolarization interval between pairs of substantially-consecutive T waves is determined. At a step 426, the maximal value of root-mean-square differences are normalized to the absolute magnitude of the signal-averaged QRS complex. At a step 428, the Lyapunov exponents are determined, in accordance with the method described above in connection to FIG. 5.

FIG. 6 depicts an exemplary EKG signal of normal morphology identifying the P, Q, R, S, and T segments of the waveform. Where other heartbeats' EKG signals might be slightly faster, the waveform morphology may be compressed into a shorter interval of time. Other heartbeats' EKG signals might also be slower, or certain segments of the waveform might be slightly different shape or length, for example a longer T-wave segment corresponds to slower repolarization. The QT interval corresponds to the time-interval between where the Q-wave begins and where the T-wave ends for each beat.

By way of example using the embodiment of FIG. 1B, fifteen subjects with a history of ventricular arrhythmia and 13 control subjects with no known risk factors for SCD were studied. There were 10 SCD events in this cohort. Two subjects had suffered confirmed out-of-hospital cardiac arrest (OHCA), including one who had been implanted previously with an ICD. Three additional long QT syndrome (LQTS) subjects were deemed high clinical risk on the basis of a personal history of syncope and a family history of at least one sudden unexplained death. The control subjects were free of known cardiovascular disease except for mild hypertension in one subject.

Using the embodiment of FIG. 1B, the QTdSI accurately predicted ventricular arrhythmias and SCD as shown in Table 1 below, where P<0.005 Fisher Exact Test, two-tailed.

TABLE 1

|  | SCD | No SCD |
|---|---|---|
| QTdSI positive | 8 | 3 |
| QTdSI negative | 2 | 15 |

In this initial example, the sensitivity of the QTdSI metric to predict SCD was 80% and the specificity was 83%. The odds-ratio was 20 and the number-needed-to-treat (NNT) was 2.

Additionally, a small sample size of cases and controls was available, so risk stratification by ejection fraction or other patient-grouping variables was not evaluated, here. In that regard, it is important to identify those patients at high risk for SCD but who do not have symptomatic left ventricular dysfunction. Secondly, some of the patients in the initial study who had dilative cardiomyopathy had comorbid atrial fibrillation, frequent ectopic beats, or had a paced rhythm and so had to be excluded from analysis. In follow-on studies, it is anticipated that specific submodels to predict SCD in the presence of those covariables will be developed. Thirdly, it should be noted that SCD is not always because of ventricular arrhythmias. For example, bradyarrhythmias and electromechanical dissociation may be a more frequent cause of SCD in nonischemic cardiomyopathies. It is thus anticipated that stability-theoretic prediction models as set forth in the present invention should be useful in these circumstances. Fourthly, the cases and controls available to us were from acute-care medical-surgical hospital-based settings.

Many different arrangements of the various components depicted, as well as components not shown, are possible without departing from the spirit and scope of the present invention. Embodiments of the present invention have been described with the intent to be illustrative rather than restrictive. Alternative embodiments will become apparent to those skilled in the art that do not depart from its scope. A skilled artisan may develop alternative means of implementing the aforementioned improvements without departing from the scope of the present invention.

It will be understood that certain features and subcombinations are of utility and may be employed without reference to other features and subcombinations and are contemplated within the scope of the claims. Not all steps listed in the various figures need be carried out in the specific order described. Accordingly, the scope of the invention is intended to be limited only by the following claims.

What is claimed is:

1. One or more computer-readable storage devices having computer-executable instructions embodied thereon that when executed, facilitate a method for automatically providing a notification for ventricular arrhythmias in an individual that are likely to result in sudden cardiac death (SCD), the method comprising:

obtaining, from one or more sensors, signals representative of electrical activity of the heart of said individual;

determining, utilizing an objective function, a QT dispersion stability index (QTdSI) from said signals, the objective function comprising a timeseries calculated from serially-acquired waveform data; the determining comprising calculating a moving average of Lyapunov exponents;

determining a difference between the determined QTdSI and a reference value to detect the presence of instability of QT interval dispersion or other measurements in said signals; and providing a notification when an increased risk for SCD is determined;

a significant difference being indicative of an increased risk of said individual of sudden cardiac death (SCD);

the results of the objective function being used by a decision-support algorithm to determine a quantitative risk for SCD; and the decision-support algorithm comprising at least one of a support vector machine, logistic regression equation, or a neural network.

2. The computer-readable storage devices of claim 1, wherein the objective function evaluates digitized electrocardiographic waveforms from one or a plurality of previous time intervals to classify a likelihood of a cascade of events leading to SCD within a future time interval.

3. The computer-readable storage devices of claim 1, wherein the Lyapunov exponent is evaluated on one or a plurality of ECG or other physiologic variables as functions of time.

4. The computer-readable storage devices of claim 1, wherein the decision-support algorithm comprises a support vector machine utilizing timeseries of calculated ECG variables including: width of root-mean-square (RMS) T-wave, total cosine T-wave dispersion, T-wave loop dispersion, normalized T-wave loop area, and relative T-wave residuum.

5. The computer-readable storage devices of claim 1, wherein the decision-support algorithm comprises a combination of two or more of a Lyapunov-based algorithm, a decision tree algorithm, or a support vector machine.

6. The computer-readable storage devices of claim 1, wherein the QTdSI is determined as a function of a continuous QT interval timeseries.

7. The computer-readable storage devices of claim 1, wherein the QTdSI is determined as a function of a discrete QT interval timeseries.

8. The computer-readable storage devices of claim 1, wherein the Lyapunov exponent is calculated for each new heart beat.

9. The computer-readable storage devices of claim 1, wherein the timeseries comprises approximately 400 samples.

10. The computer-readable storage devices of claim 1, wherein the objective function comprises a second-order polynomial function determined using Taylor series regression or spectral analysis.

11. A method for automatically providing a notification for ventricular arrhythmias in an individual that are likely to result in sudden cardiac death (SCD), the method comprising:

obtaining, from one or more sensors, ECG signals representative of electrical activity of the heart of said individual; and determining, utilizing an objective function, a QT dispersion stability index (QTdSI) from said signals, the objective function comprising a timeseries calculated from serially-acquired waveform data as functions of time the determining comprising calculating a moving average of Lyapunov exponents of a plurality of ECG or other physiologic variables;

determining a difference between the determined QTdSI and a reference value to detect the presence of instability of QT interval dispersion or other measurements in said signals;

a significant difference being indicative of an increased risk of said individual of SCD; and providing a notification to a health care provider when said increased risk for SCD is indicated;

the results of the objective function being used by a decision-support algorithm to determine a quantitative risk for SCD; and the decision-support algorithm comprising at least one of a support vector machine, logistic regression equation, or a neural network.

12. The method of claim 11, wherein the objective function evaluates digitized electrocardiographic waveforms from one or a plurality of previous time intervals to classify a likelihood of a cascade of events leading to SCD within a future time interval.

13. The method of claim 11, wherein the decision-support algorithm comprises a support vector machine utilizing timeseries of calculated ECG variables including: width of root-mean-square (RMS) T-wave, total cosine T-wave dispersion, T-wave loop dispersion, normalized T-wave loop area, and relative T-wave residuum.

14. The method of claim 11, wherein the decision-support algorithm comprises a combination of two or more of a Lyapunov-based algorithm, a decision tree algorithm, or a support vector machine.

15. The method of claim 11, wherein the QTdSI is determined as a function of a continuous QT interval timeseries.

16. The method of claim 11, wherein the QTdSI is determined as a function of a discrete QT interval timeseries.

* * * * *